(12) United States Patent
Peng et al.

(10) Patent No.: US 10,487,062 B1
(45) Date of Patent: Nov. 26, 2019

(54) REGIOSELECTIVE ONE-STEP PROCESS FOR SYNTHESIZING 2-HYDROXYQUINOXALINE

(71) Applicant: DEVELOPMENT CENTER FOR BIOTECHNOLOGY, Taipei (TW)

(72) Inventors: Shao-Zheng Peng, Taipei (TW); Yuan-Ting Cho, Taipei (TW); Pao-Chiung Hong, Taipei (TW)

(73) Assignee: DEVELOPMENT CENTER FOR BIOTECHNOLOGY, Taipei (TW)

( * ) Notice: Subject to any disclaimer, the term of this patent is extended or adjusted under 35 U.S.C. 154(b) by 0 days.

(21) Appl. No.: 16/529,371

(22) Filed: Aug. 1, 2019

Related U.S. Application Data

(60) Provisional application No. 62/713,661, filed on Aug. 2, 2018.

(51) Int. Cl.
C07D 241/52 (2006.01)
C07D 241/44 (2006.01)

(52) U.S. Cl.
CPC ......... *C07D 241/44* (2013.01); *C07D 241/52* (2013.01)

(58) Field of Classification Search
CPC .................................................. C07D 241/52
USPC .................................................. 544/354, 353
See application file for complete search history.

(56) References Cited

U.S. PATENT DOCUMENTS 5,169,955 A 12/1992 Kobayashi et al.

FOREIGN PATENT DOCUMENTS

| WO | 2006134378 A1 | 12/2006 |
| WO | 2010054229 A1 | 5/2010 |
| WO | 2014139325 A1 | 9/2014 |

OTHER PUBLICATIONS

Pedron et al., "Novel 8-nitroquinolin-2(1H)-ones as NTR-bioactivated antikinetoplastid molecules: Synthesis, electrochemical and SAR study", Published in European journal of medicinal chemistry 2018, 18 pages provided.

*Primary Examiner* — Venkataraman Balasubramanian
(74) *Attorney, Agent, or Firm* — Hamre, Schumann, Mueller & Larson, P.C.

(57) ABSTRACT

A regioselective one-step process for the synthesis of 2-hydroxyquinoxaline of Formula (1) or tautomers thereof:

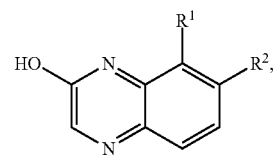

Formula (1)

comprising reacting 1,2-phenylenediamine of Formula (2):

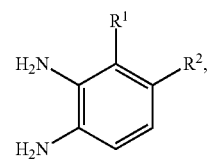

Formula (2)

with an excess amount of glyoxylic acid, glyoxylic acid monohydrate, or a 2,2-dialkoxyacetic acid of Formula (3):

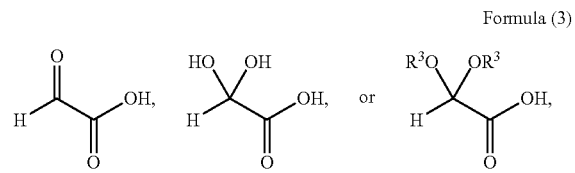

Formula (3)

at a low temperature;
wherein $R^1$ and $R^2$ are as defined in the specification.

9 Claims, No Drawings

REGIOSELECTIVE ONE-STEP PROCESS FOR SYNTHESIZING 2-HYDROXYQUINOXALINE

CROSS REFERENCE TO RELATED APPLICATIONS

This application claims priority to U.S. Provisional Application No. 62/713,661, filed Aug. 2, 2018; the disclosure of which is incorporated herein by reference in its entirety.

FIELD OF THE INVENTION

The present invention provides a regioselective one-step process for the synthesis of 2-hydroxyquinoxaline of Formula (1) or tautomers thereof from 1,2-phenylenediamine of Formula (2).

BACKGROUND OF THE INVENTION

Quinoxaline moiety is a common component in a variety of biologically active drug-like molecules and has been found to be useful in the treatment of abnormal cell growth, such as cancer, in mammals. Hydroxyquinoxaline derivatives can be used as intermediates for the preparation of quinoxaline moiety and can be easily prepared from 1,2-phenylenediamine.

However, reactions of 3,4-disubstituted-1,2-phenylenediamine derivatives with glyoxylate or glyoxylic acid usually provide non-selective mixtures of 2-hydroxy-7,8-disubstitutedquinoxalines and regioisomeric 2-hydroxy-5,6-disubstitutedquinoxalines (Scheme A). These reactions are of limited utility not only due to their lack of regioselectivity and impact on overall yield, but also due to separation of the resulting isomers being generally extremely difficult and possibly requiring preparative chromatography, an often undesirable step in process sequence.

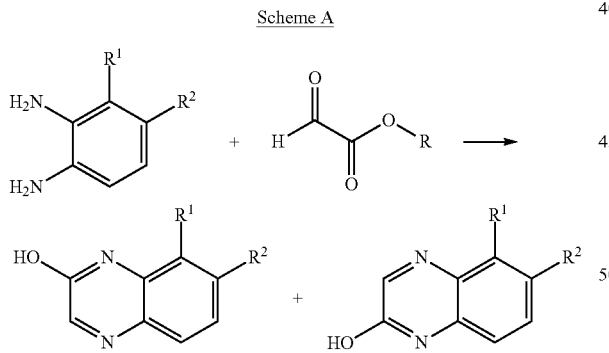

Scheme A

For example, PCT patent publications WO 2006/134378 A1, WO 2010/054229 A1, and WO 2014/139325 A1, and an article in the European Journal of Medicinal Chemistry (2018), 155, 135-152 describe quinoxaline derivatives and their uses as bioactivity agents. The preparation of such compounds involves synthesis of hydroxyquinoxaline as an intermediate by condensation of 1,2-phenylenediamine with glyoxylate or glyoxylic acid. The reaction usually provides a non-selective mixture of regioisomers of the desired product.

WO 2006/134378 A1, on page 138, describes a reaction that provides a mixture of isomers. Briefly, 3,4-Difluorobenzene-1,2-diamine (4.6 g, 31.6 mmol) and ethyl oxoacetate (50 wt % in toluene, 13.0 mL, 63.2 mmol) were reacted to give a mixture product of 3.7 g with 30% of the regioisomer 5,6-difluoroquinoxalin-2(1H)-one. (Scheme B).

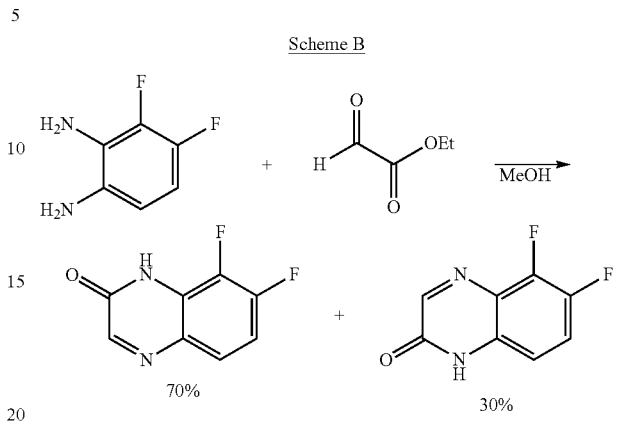

Scheme B

WO 2010/054229 A1, on page 92, describes the preparation of hydroxyquinoxaline derivatives. Such a reaction provides a mixture of isomers. Briefly, 3-chlorobenzene-1,2-diamine (3.60 g, 25.3 mmol) and ethyl glyoxylate solution (50% in toluene; 6.0 mL, 30.3 mmol) were heated in ethanol (87 mL) to 75° C. for 18 hours. The reactants were then placed in a refrigerator to be cooled and the product was filtered to give 5-chloroquinoxalin-2(1H)-one as a rust colored solid (3.42 g). This crude product was purified by supercritical fluid chromatography to give 5-chloroquinoxalin-2(1H)-one and 8-chloroquinoxalin-2(1H)-one (Scheme C).

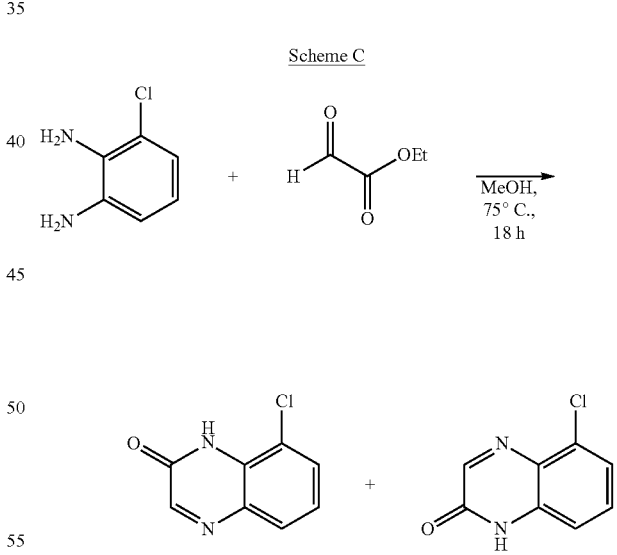

Scheme C

WO 2014/139325 A1, on pages 257 and 258, describes the preparation of hydroxyquinoxaline derivatives as intermediates. Such a reaction provides a mixture of isomers. Briefly, to a stirred suspension of ethyl 4-(2,3-diaminophenylsulfonamido) benzoate (5 g, 15 mmol) in ethanol (50 mL) was added a solution of ethyl glyoxylate in toluene (1.6 M, 3 mL, 18 mmol) over a period of 5 min. After heating to 45° C. for 10 h, the mixture was left at r.t. under stirring. The resulting product was a mixture of regioisomers (Scheme D).

Scheme D

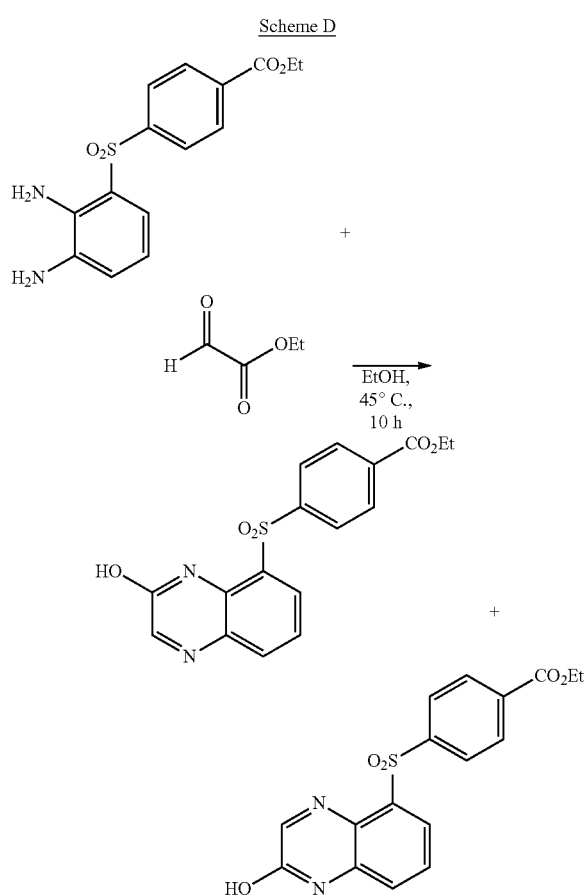

European Journal of Medicinal Chemistry (2018), 155, 135-152, describes the preparation of hydroxyquinoxaline derivatives as intermediates, with such a reaction providing a mixture of isomers (Scheme E).

Scheme E

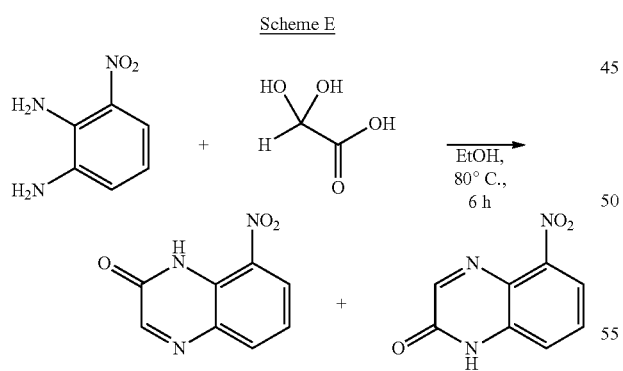

In addition, U.S. Pat. No. 5,169,955 discloses a process for producing a hydroquinoxaline which may be substituted with one or more substituents selected from the group consisting of halogen, lower alkyl, and lower alkoxy. The process comprises reacting o-phenylenediamine which may be substituted with one or more substituents selected from the group consisting of halogen, lower alkyl, and lower alkoxy with glyoxylic acid in a lower aliphatic alcohol solvent without using a catalyst.

These procedures, however, have the disadvantage of having low regioselectivity. The lack of regioselectivity requires the separation of the two regioisomers, considerably increasing production costs. It would be desirable to have a process for regioselective preparation of hydroxyquinoxaline.

SUMMARY OF THE INVENTION

The present invention provides a regioselective one-step process for the synthesis of 2-hydroxyquinoxaline of Formula (1) or tautomers thereof from 1,2-phenylenediamine of Formula (2). It was surprisingly found that by slowly adding 1,2-phenylenediamine of Formula (2) to an excess amount of glyoxylic acid, glyoxylic acid monohydrate or a 2,2-dialkoxyacetic acid of Formula (3) at a low temperature, 2-hydroxyquinoxalines of Formula (1) or tautomers thereof can be regioselectively produced (Scheme F):

Scheme F

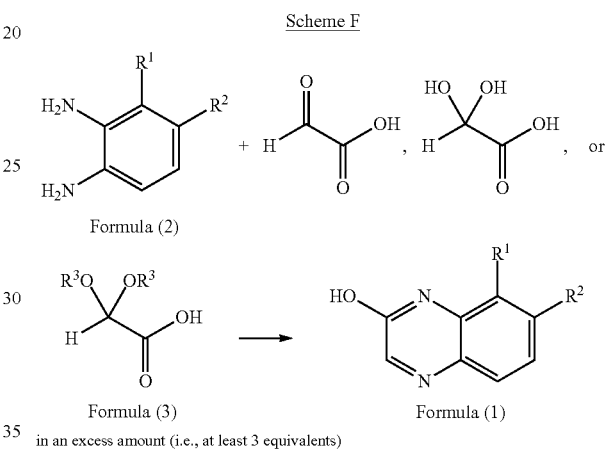

in an excess amount (i.e., at least 3 equivalents)

wherein $R^1$ and $R^2$ are as defined herein.

DETAILED DESCRIPTION OF THE INVENTION

The present invention provides a regioselective one-step process for the synthesis of 2-hydroxyquinoxaline of Formula (1) or tautomers thereof:

Formula (1)

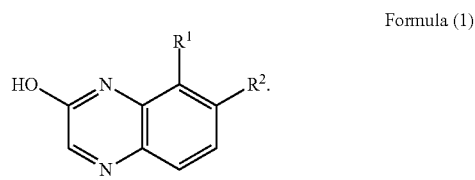

The process of the invention comprises reacting 1,2-phenylenediamine of Formula (2)

Formula (2)

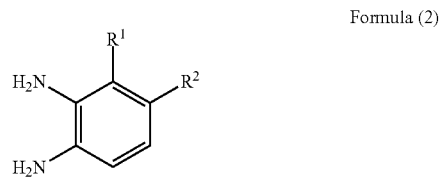

with an excess amount of glyoxylic acid, glyoxylic acid monohydrate, or a 2,2-dialkoxyacetic acid of Formula (3):

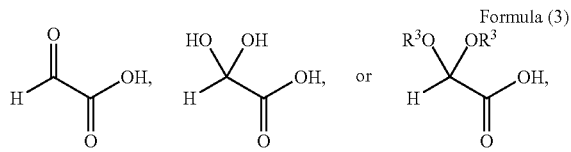

at a low temperature ranging from about −20° C. to about 5° C.;
wherein
$R^1$ is selected from the group consisting of $NO_2$, CN, $CO_2R^4$, $CONR^5R^6$, $CF_3$, and halogen;
$R^2$ is selected from the group consisting of hydrogen, alkyl, and halogen;
$R^3$ is $C_1$-$C_3$ alkyl, or two $R^3$ groups, together with the oxygen atoms to which they are bound, form a 5-, 6-, or 7-membered O-containing heterocyclic ring;
$R^4$ is $C_1$-$C_6$ alkyl, optionally substituted with one or more groups selected from the group consisting of halogen, R', OR', and SR'; or represents $C_3$-$C_6$ cycloalkyl, $C_6$-$C_{10}$ aryl, or $C_7$-$C_{12}$ arylalkyl, all of which being optionally substituted by one or more groups selected from the group consisting of halogen, R', OR', and SR';
$R^5$ and $R^6$, which can be the same or different, are independently selected from the group consisting of hydrogen, $C_1$-$C_6$ alkyl, $C_6$-$C_{10}$ aryl group, and $C_7$-$C_{12}$ arylalkyl, or $R^5$ and $R^6$, together with the nitrogen atom to which they are bound, form a 5-, 6-, or 7-membered N-containing heterocyclic ring; and
R' is alkyl.

Unless specifically specified, the term "alkyl" used herein refers to a branched or straight-chain monovalent hydrocarbon radical having one to eight carbon atoms. The alkyl group is preferably $C_1$ to $C_6$, more preferably $C_1$ to $C_4$. Examples of a $C_1$-$C_6$ alkyl group include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "halogen" refers to F, Cl, Br or I. Preferably, it is F, Cl, or Br.

The term "cycloalkyl" used herein refers to a saturated monovalent mono-cyclic hydrocarbon radical of three to seven ring carbons. Examples of "cycloalkyl" include cyclopropyl, cyclobutyl, cyclopentyl, and cyclohexyl.

The term "aryl" is used to mean a mono- or polycyclic aromatic ring system in which the rings are carbocyclic and have six to twelve ring carbons. Examples of aryl groups are phenyl, naphthyl, and the like.

The term "arylalkyl" refers to an aryl bound with an alkyl.

A saturated 5-, 6-, or 7-membered N-containing heterocyclic ring used herein refers to a monovalent monocyclic non-aromatic ring system or monovalent polycyclic ring system that contains one N atom and the remaining ring atoms are either carbon atoms or additional heteroatoms. The ring may contain one nitrogen atom and one or more additional heteroatoms selected from N, O, and S, or no additional heteroatoms. Examples of such a 5-, 6-, or 7-membered N-containing heterocyclic ring include, but are not limited to, piperidine, piperazine, morpholine, and pyrrolidine. The ring is unsubstituted or substituted on one or more ring carbon atoms and/or on any additional heteroatom present in the ring.

A saturated 5-, 6-, or 7-membered O-containing heterocyclic ring used herein refers to a monovalent monocyclic non-aromatic ring system or monovalent polycyclic ring system that contains two O atoms and the remaining ring atoms are either carbon atoms or additional heteroatoms. The ring may contain two oxygen atoms and one or more additional heteroatoms selected from N, O, and S, or no additional heteroatoms. Examples of such a saturated 5-, 6-, or 7-membered O-containing heterocyclic ring include, but are not limited to, 1,3-dioxolane, 1,3-dioxane, and 1,3-dioxepane.

The term "optionally substituted" means that the group may or may not be substituted by one or more substituents. Substituents for a substituted group include, but are not limited to halo, alkyl, alkoxy, amino, haloalkyl, —S-alkyl, alkyl-aryl, and the like.

The term "tautomer" means that the compound may exist in tautomeric forms, including the amide and imidic acid form, and mixtures thereof. The preparation of all such tautomeric forms is included within the scope of the present invention. Tautomers exist as mixtures of a tautomeric set in solution. In solid form, usually one tautomer predominates. Even though the preparation of one tautomer may be described, the present invention encompasses the preparation of all tautomers of the present compounds.

In the present invention, the 1,2-phenylenediamine of Formula (2) is provided in the form of a solution with a suitable solvent(s); and the glyoxylic acid, glyoxylic acid monohydrate, or a 2,2-dialkoxyacetic acid of Formula (3) is provided in the form of a solution with a suitable solvent(s). In an embodiment of the invention, the solution of 1,2-phenylenediamine of Formula (2) is slowly added (e.g., dropwise) into the solution of glyoxylic acid, glyoxylic acid monohydrate, or a 2,2-dialkoxyacetic acid of Formula (3) at the low temperature to obtain a desired, regioselectively produced product.

Examples of the low temperature used in the process of the invention include, but are not limited to, about −20° C., about −19° C., about −18° C., about −17° C., about −16° C., about −15° C., about −14° C., about −13° C., about −12° C., about −11° C., about −10° C., about −9° C., about −8° C., about −7° C., about −6° C., about −5° C., about −4° C., about −3° C., about −2° C., about −1° C., about 0° C., about 1° C., about 2° C., about 3° C., about 4° C., and about 5° C. Preferably, the low temperature is about 0° C.

Any suitable solvents can be used to prepare the solution of 1,2-phenylenediamine of Formula (2) and the solution of glyoxylic acid, glyoxylic acid monohydrate, or a 2,2-dialkoxyacetic acid of Formula (3). Examples of the solvents include, but are not limited to, aliphatic or cycloaliphatic hydrocarbons (e.g., petroleum ether, hexane, cyclohexane, etc.), chlorinated hydrocarbons (e.g., methylene chloride, chloroform, dichloroethane, etc.), aromatic hydrocarbons (e.g., benzene, toluene, xylene, chlorobenzene, etc.), ethers (e.g., diethyl ether, diisopropyl ether, dimethoxyethane, dioxane, tetrahydrofuran, etc.), alcohols and glycols (e.g., methanol, ethanol, iso-propanol, methyl cellosolve, ethylene glycol, etc.), nitriles (e.g., acetonitrile, benzonitrile, etc.), aprotic dipolar solvents (e.g., dimethylformamide, dimethylacetamide, hexamethylphosphoric triamide, sulfoxide, sulfolane, N-methyl-pyrrolidone, etc.), and water.

The phrase "in an excess amount" means that glyoxylic acid, glyoxylic acid monohydrate, or a 2,2-dialkoxyacetic acid of Formula (3) is used in an amount of at least 3 molar equivalents relative to per molar equivalent of a 1,2-phenylenediamine of Formula (2). Preferably, the glyoxylic acid, the glyoxylic acid monohydrate, or the 2,2-dialkoxyacetic acid of Formula (3) is used in an amount of at least 4 molar equivalents relative to per molar equivalent of the 1,2-phenylenediamine of Formula (2). More preferably, the glyoxylic acid, the glyoxylic acid monohydrate, or the 2,2-dialkoxyacetic acid of Formula (3) is used in an amount of at least 5 molar equivalents relative to per molar equivalent of the 1,2-phenylenediamine of Formula (2).

Preferably, the 2-hydroxyquinoxaline of Formula (1) is 7-chloro-2-hydroxyquinoxaline-8-carbonitrile, 7,8-difluoroquinoxalin-2-ol, methyl 2-hydroxyquinoxaline-8-carboxylate, 8-nitroquinoxalin-2-ol, 8-(trifluoromethyl) quinoxalin-2-ol, 8-chloroquinoxalin-2-ol, 8-bromoquinoxalin-2-ol, or tautomers thereof.

The reaction has regioselectivity of more than 90%, preferably, more than 95%, or more preferably, more than 99%.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

In addition to achieving an excellent regioselectivity, the process is advantageous because it can be carried out under conditions that are easily operated in both laboratories and industrial plants so as to achieve a high yield and a high purity of the 2-hydroxyquinoxaline of Formula (1) or tautomers thereof.

The invention will be further described in the Examples as follows. The examples given below are intended to be illustrative only and not to limit the invention. Any modifications and variations that can be easily made by those skilled in the art fall within the scope of the disclosure of the specification and the appended claims of the present invention. The purity of the product and regioselectivity of the reaction were determined by the HPLC method.

EXAMPLES

Example 1

General Method: Preparation of 7-chloro-2-hydroxyquinoxaline-8-carbonitrile

To a stirred solution of glyoxylic acid monohydrate (2,473 mg, 26.87 mmol, 4.5 eq) in methanol (50 mL) was added dropwise a solution of 2,3-diamino-6-chlorobenzonitrile (1,000 mg, 5.97 mmol, 1.0 eq) in methanol (250 ml) at 0° C. After being stirred at the same temperature as above, the starting material was consumed as indicated by TLC analysis ($CH_2Cl_2$/MeOH=20/1, Rf=0.4). The reaction mixture was then filtered, and the precipitate was washed with methanol to give 7-chloro-2-hydroxyquinoxaline-8-carbonitrile as a light yellow solid (1044 mg, yield: 85%, purity: 98.8%). The regioselectivity of the reaction is 98.7%. $^1$H NMR (600 MHz, DMSO-d6) δ 13.15 (s, 1H), 8.43 (s, 1H), 8.15 (d, J=7.5 Hz, 1H), 7.70 (s, 1H). LCMS (ESI) m/z [M]$^+$ calcd for $C_9H_4ClN_3O$: 205.00; found: 205.73.

Compounds of the following Examples were synthesized following the above General Method with a variety of other substituted 1,2-phenylenediamines.

Example 2

7,8-difluoroquinoxalin-2-ol (purity: 95.4%) $^1$H NMR (500 MHz, DMSO-d6) δ 12.83 (br, 1H), 8.18 (s, 1H), 7.85-7.52 (m, 1H), 7.37 (dd, J=18.1, 9.0 Hz, 1H). $^{13}$C NMR (150 MHz, DMSO-d6) δ 155.0, 152.2, 151.3, 149.7, 130.0, 125.6, 123.6, 111.7. LCMS (ESI) m/z [M]+ calcd for $C_8H_4F_2N_2O$: 182.03; found: 182.12. The regioselectivity of the reaction is 92.6%.

Example 3

8-(trifluoromethyl)quinoxalin-2-ol (purity: 99.7%)$^1$H NMR (500 MHz, CDCl$_3$) δ 9.12 (s, 1H), 8.38 (s, 1H), 8.10 (d, J=8.1 Hz, 1H), 7.85 (d, J=7.8 Hz, 1H), 7.45 (t, J=7.9 Hz, 1H), 7.28 (s, 1H). $^{13}$C NMR (125 MHz, CDCl$_3$) δ 153.9, 152.0, 134.2, 133.1, 128.4, 124.5, 123.3, 122.3, 115.6. LCMS (ESI) m/z [M+H]$^+$ calcd for $C_9H_6F_3N_2O$: 215.04; found: 215.30. The regioselectivity of the reaction is 93.0%.

Example 4

8-nitroquinoxalin-2-ol (purity: 99.9%)$^1$H NMR (600 MHz, DMSO-d6) δ 11.60 (s, 1H), 8.41 (d, J=8.2 Hz, 1H), 8.36 (s, 1H), 8.22 (dd, J=7.9, 1.4 Hz, 1H), 7.51 (t, J=8.0 Hz, 1H). $^{13}$C NMR (125 MHz, CDCl3) δ 154.3, 153.4, 136.5, 134.8, 133.7, 127.9, 127.5, 123.1. LCMS (ESI) m/z [M+H]$^+$ calcd for $C_8H_6N_3O_3$: 192.03; found: 192.00. The regioselectivity of the reaction is 99.9%.

Example 5 methyl 2-hydroxyquinoxaline-8-carboxylate (purity: 97.9%) $^1$H NMR (500 MHz, DMSO-d6) δ 11.59 (s, 1H), 8.32 (d, J=2.2 Hz, 1H), 8.21 (dd, J=7.9, 1.3 Hz, 1H), 8.12 (dd, J=8.0, 1.3 Hz, 1H), 7.46 (t, J=7.9 Hz, 1H), 3.96 (s, 3H). $^{13}$C NMR (125 MHz, CDCl$_3$) δ 167.0, 154.0, 152.5, 135.1, 133.2, 132.9, 132.8, 123.3, 114.1, 53.3. LCMS (ESI) m/z [M+H]$^+$ calcd for $C_{10}H_9N_2O_3$: 205.05; found: 205.41. The regioselectivity of the reaction is 94.8%.

Example 6

8-chloroquinoxalin-2-ol (purity: 99.9%) $^1$H NMR (600 MHz, DMSO-d6) δ 12.04 (s, 1H), 8.23 (s, 1H), 7.77 (d, J=7.9 Hz, 1H), 7.70 (d, J=7.7 Hz, 1H), 7.32 (t, J=7.4 Hz, 1H). 13C NMR (125 MHz, DMSO-d6) δ 155.7, 153.2, 133.6, 131.2, 129.7, 128.5, 124.1, 119.1. LCMS (ESI) m/z [M+H]$^+$ calcd for $C_8H_6ClN_2O$: 181.01; found: 181.10. The regioselectivity of the reaction is 91.8%.

Example 7

8-bromoquinoxalin-2-ol (purity: 99.2%) $^1$H NMR (600 MHz, DMSO-d6) δ 11.72 (s, 1H), 8.23 (s, 1H), 7.88 (d, J=7.5 Hz, 1H), 7.83 (d, J=7.9 Hz, 1H), 7.29 (t, J=7.3 Hz, 1H). $^{13}$C NMR (125 MHz, CDCl$_3$) δ 155.9, 153.1, 134.6, 133.8, 130.8, 129.2, 124.8, 108.6. LCMS (ESI) m/z [M+H]$^+$ calcd for $C_8H_6BrN_2O$: 224.97, found: 224.85 [M+H]$^+$. The reaction regioselectivity is 94.3%.

Example 8

Comparative Test: 1.2 Eq Glyoxylic Acid Monohydrate

Preparation of 7,8-difluoroquinoxalin-2-ol

To a mixture of glyoxylic acid monohydrate (76.2 mg, 0.83 mmol, 1.2 eq) and 3,4-difluorobenzene-1,2-diamine (100 mg, 0.69 mmol, 1.0 eq) was added cold methanol (62.0 mL) at −15° C. The obtained reaction solution was stirred for 2 hours, and 3,4-difluorobenzene-1,2-diamine was consumed as indicated by TLC analysis. The reaction mixture was then concentrated, dissolved in 10% DMSO, diluted with MeOH, and monitored by HPLC analysis. The ratio of 7,8-difluoroquinoxalin-2-ol and 5,6-difluoroquinoxalin-2-ol is 1.4:1.0, and the regioselectivity of the reaction is 58.3%.

Example 9

Comparative Test: 1.2 Eq Ethyl Glyoxylate

Preparation of 7,8-difluoroquinoxalin-2-ol

To a solution containing 3,4-difluorobenzene-1,2-diamine (100 mg, 0.69 mmol, 1.0 eq) and ethyl glyoxylate solution (50% in toluene; 0.83 mmol, 1.2 eq) was added methanol (62 mL), and the resulting solution was refluxed for 18 hours. The obtained crude product was concentrated, dissolved in 10% DMSO, diluted with MeOH, and monitored by HPLC analysis. The ratio of 7,8-difluoroquinoxalin-2-ol and 5,6-difluoroquinoxalin-2-ol is 1.1:1.0, and the regioselectivity of the reaction is 51.8%.

What is claimed is:

1. A regioselective one-step process for the synthesis of 2-hydroxyquinoxaline of Formula (1) or tautomers thereof:

Formula (1)
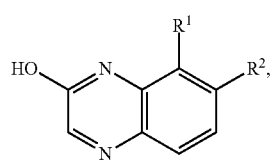

comprising reacting 1,2-phenylenediamine of Formula (2):

Formula (2)
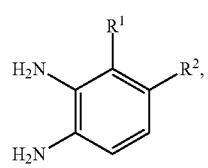

with an excess amount of glyoxylic acid, glyoxylic acid monohydrate, or a 2,2-dialkoxyacetatic of Formula (3):

Formula (3)
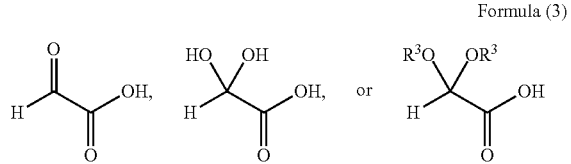

at a low temperature ranging from about −20° C. to about 5° C.;

wherein
$R^1$ is selected from the group consisting of $NO_2$, CN, $CO_2R^4$, $CONR^5R^6$, $CF_3$, and halogen;
$R^2$ is selected from the group consisting of hydrogen, alkyl, and halogen;
$R^3$ is $C_1$-$C_3$ alkyl; or two $R^3$ groups, together with the oxygen atoms to which they are bound, form a 5-, 6-, or 7-membered O-containing heterocyclic ring;
$R^4$ is $C_1$-$C_6$ alkyl, optionally substituted with one or more groups selected from the group consisting of halogen, R', OR', and SR'; or represents $C_3$-$C_6$ cycloalkyl, $C_6$-$C_{10}$ aryl, or $C_7$-$C_{12}$ arylalkyl, all of which being optionally substituted by one or more groups selected from the group consisting of halogen, R', OR', and SR';
$R^5$ and $R^6$, which can be the same or different, are independently selected from the group consisting of hydrogen, $C_1$-$C_6$ alkyl, $C_6$-$C_{10}$ aryl, and $C_7$-$C_{12}$ arylalkyl; or
$R^5$ and $R^6$, together with the nitrogen atom to which they are bound, form a 5-, 6-, or 7-membered N-containing heterocyclic ring; and
R' is alkyl.

2. The process according to claim 1, wherein a 1,2-phenylenediamine of Formula (2) is provided in the form of a solution with a suitable solvent; and wherein glyoxylic acid, glyoxylic acid monohydrate, or a 2,2-dialkoxyacetic acid of Formula (3) is provided in the form of a solution with a suitable solvent.

3. The process according to claim 2, wherein the solution of a 1,2-phenylenediamine of Formula (2) is added into the solution of glyoxylic acid, glyoxylic acid monohydrate, or a 2,2-dialkoxyacetic acid of Formula (3).

4. The process according to claim 1, wherein the low temperature is about 0° C.

5. The process according to claim 1, wherein the excess amount of glyoxylic acid, glyoxylic acid monohydrate, or a 2,2-dialkoxyacetic acid of Formula (3) is at least 3 molar equivalents relative to per molar equivalent of a 1,2-phenylenediamine of Formula (2).

6. The process according to claim 4, wherein the excess amount of glyoxylic acid, glyoxylic acid monohydrate, or a 2,2-dialkoxyacetic acid of Formula (3) is at least 4 molar equivalents relative to per molar equivalent of a 1,2-phenylenediamine of Formula (2).

7. The process according to claim 2, wherein the suitable solvents used to prepare the solution of 1,2-phenylenediamine of Formula (2) and the solution of glyoxylic acid, glyoxylic acid monohydrate, or a 2,2-dialkoxyacetic acid of Formula (3) are organic solvents.

8. The process according to claim 7, wherein the organic solvent is selected from the group consisting of methanol, ethanol, isopropanol, acetonitrile, dichloromethane, toluene, tetrahydrofuran, and a mixture thereof.

9. The process according to claim 1, wherein the 2-hydroxyquinoxaline of Formula (1) is 7-chloro-2-hydroxyquinoxaline-8-carbonitrile, 7,8-difluoroquinoxalin-2-ol, methyl 2-hydroxyquinoxaline-8-carboxylate, 8-nitroquinoxalin-2-ol, 8-(trifluoromethyl) quinoxalin-2-ol, 8-chloroquinoxalin-2-ol, 8-bromoquinoxalin-2-ol, or tautomers thereof.

* * * * *